(12) United States Patent
Diefenbacher et al.

(10) Patent No.: US 8,196,755 B2
(45) Date of Patent: Jun. 12, 2012

(54) PROCESS FOR PRODUCING A COMPOSITE MEMBRANE

(75) Inventors: Armin Diefenbacher, Freisbach (DE); Hartwig Voss, Frankenthal (DE); Gunter Schuch, Ludwigshafen (DE); Manfred Noack, Berlin (DE); Ingolf Voigt, Jena (DE); Hannes Richter, Hermsdorf (DE); Juergen Caro, Berlin (DE)

(73) Assignee: BASF SE, Ludwigshafen (DE)

( * ) Notice: Subject to any disclaimer, the term of this patent is extended or adjusted under 35 U.S.C. 154(b) by 326 days.

(21) Appl. No.: 12/304,773

(22) PCT Filed: May 21, 2007

(86) PCT No.: PCT/EP2007/054875
§ 371 (c)(1),
(2), (4) Date: Apr. 15, 2009

(87) PCT Pub. No.: WO2007/144247
PCT Pub. Date: Dec. 21, 2007

(65) Prior Publication Data
US 2009/0200236 A1      Aug. 13, 2009

(30) Foreign Application Priority Data
Jun. 13, 2006   (EP) .................................... 06115334

(51) Int. Cl.
*B01D 39/00*   (2006.01)
*B01D 29/00*   (2006.01)
*B29C 65/00*   (2006.01)
*B29C 44/04*   (2006.01)

(52) U.S. Cl. ................ 210/500.25; 210/490; 264/41; 264/42; 264/45.1; 502/4; 502/64

(58) Field of Classification Search ............. 210/500.25, 210/490, 640; 55/523, 524; 95/45, 52; 264/42, 264/45.1, 41; 502/4, 60, 86, 63
See application file for complete search history.

(56) References Cited

U.S. PATENT DOCUMENTS

| | | | |
|---|---|---|---|
| 5,258,339 A | | 11/1993 | Ma et al. |
| 5,968,366 A | * | 10/1999 | Deckman et al. ............. 210/651 |
| 6,090,289 A | * | 7/2000 | Verduijn et al. ............. 210/644 |
| 6,140,263 A | | 10/2000 | Anstett et al. |
| 6,177,373 B1 | | 1/2001 | Sterte et al. |
| 6,197,427 B1 | | 3/2001 | Anstett et al. |
| 6,494,326 B1 | | 12/2002 | Nenoff et al. |
| 6,974,457 B2 | * | 12/2005 | Gibson ........................... 606/41 |
| 7,049,259 B1 | * | 5/2006 | Deckman et al. ................. 502/4 |
| 7,252,876 B2 | * | 8/2007 | Mori et al. ................. 428/312.2 |
| 7,749,414 B2 | * | 7/2010 | Bitterlich et al. ............. 264/45.1 |
| 7,815,712 B2 | * | 10/2010 | Liu et al. ........................... 95/45 |
| 7,973,090 B2 | * | 7/2011 | Suzuki et al. ................... 521/27 |
| 2004/0229027 A1 | * | 11/2004 | Mori et al. ..................... 428/212 |
| 2007/0137485 A1 | | 6/2007 | Bitterlich et al. |

FOREIGN PATENT DOCUMENTS

| | | |
|---|---|---|
| DE | 10 2004 001974 | 8/2005 |
| EP | 0 481 660 | 4/1992 |
| WO | 00 20105 | 4/2000 |

OTHER PUBLICATIONS

Poshusta, J.C. et al., "Temperature and Pressure Effects on $CO_2$ and $CH_4$ Permeation Through MFI Zeolite Membranes", Journal of Membrane Science, vol. 160, pp. 115-125 (1999).
Wong, W.C. et al., "Effects of Synthesis Parameters on the Zeolite Membrane Morphology", Journal of Membrane Science, vol. 193, pp. 141-161 (2001).
Vroon, Z.A.E.P. et al., "Preparation and Characterization of Thin Zeolite MFI Membranes on Porous Supports", Journal of Membrane Science, vol. 144, pp. 65-76 (1998).
Kusakabe, K. et al., "Preparation of MFI-Type Zeolite Membranes and Their Use in Separating $n$-Butane and $i$-Butane", Journal of Chemical Engineering of Japan, vol. 30, No. 1, pp. 72-78 (1997).
Lin, X. et al., "Parallel Pathways for Transport in ZSM-5 Zeolite Membranes", Chem. Mater., vol. 10, pp. 3716-3723 (1998).
Nomura, M. et al., "Transport Phenomena Through Intercrystalline and Intracrystalline Pathways of Silicalite Zeolite Membranes", Journal of Membrane Science, vol. 187, pp. 203-212 (1999).
Xomeritakis, G. et al., "Separation of Xylene Isomer Vapors With Oriented MFI Membranes MadebySeededGrowth", Ind. Eng. Chem. Res., vol. 40, pp. 544-552 (2001).
U.S. Appl. No. 12/867,503, filed Aug. 13, 2010, Birnbach, et al.

* cited by examiner

*Primary Examiner* — Ana Fortuna
(74) *Attorney, Agent, or Firm* — Oblon, Spivak, McClelland, Maier & Neustadt, L.L.P.

(57) ABSTRACT

A process for the production of a composite membrane, one or more microporous separation layers comprising a zeolite of the MFI type being produced by hydrothermal synthesis on a porous substrate, wherein one or more additives from the group consisting of linear ($C_1$-$C_4$)-alcohols, ammonia, primary, secondary and tertiary amines having in each case ($C_1$-$C_4$)-alkyl radicals, ($C_1$-$C_4$)-aminoalcohols and ($C_3$-$C_4$)-ketones are added to the synthesis solution for the hydrothermal synthesis.

10 Claims, No Drawings

PROCESS FOR PRODUCING A COMPOSITE MEMBRANE

CROSS-REFERENCE TO RELATED APPLICATIONS

The present application is a 35 U.S.C. §371 National Stage patent application of International patent application PCT/EP07/54875, filed on May 21, 2007, which claims priority to German patent application 06115334.2, filed on Jun. 13, 2006.

The invention relates to a process for the production of a composite membrane which comprises at least one porous substrate and a microporous separation layer which comprises a zeolite of the MFI type, a membrane obtainable by the process and the use thereof for gas separation and pervaporation.

Processes for the production of composite membranes are known. The production of such membranes is generally carried out in such a way that the substrate is brought into contact with a solution (synthesis solution) which comprises components from which the separation layer is formed in a chemical reaction (synthesis).

It is reported (e.g. in Poshuta et al., J. of Membrane Science 160 (1999), pages 115-125, or Wong et al., J. of Membrane Science 193 (2001), pages 141-161) that great value is to be attached to the production of defect-free zeolite layers since the defects give rise to unselective flow outside the zeolite pores.

It was proposed to eliminate these defects, for example, by a second membrane synthesis on the membrane comprising defects (e.g. Vroon et al., J. of Membrane Science 144 (1998), pages 65-76) or by aftertreatment of the defects in a sol gel process (e.g. U.S. Pat. No. 6,494,326).

In addition, Kusakabe et al. in J. of Chem. Eng. of Jap. 30 (1997), pages 72-78 derive, from permeation measurements using various individual gases, that not only do defects in the zeolite layer adversely affect the permeance and the permselectivity of a membrane but also the intergrowth of the particle boundaries of the zeolite crystallites influences the permeation properties. It is concluded that gaps at these particle boundaries have to be avoided in order to increase the selectivity. However, the manner in which this can be achieved is not described.

Lin et al. report, in Chem. Mater. 10 (1998) 3716-3723, high n-butane/isobutane selectivities of membranes which have not only zeolite but also nonzeolite pores. The selectivity is due to the small size or concentration of the nonzeolite pores.

Nomura et al. state, in J. of Membrane Science 187 (2001), pages 203-212, that, in the case of zeolite membranes, mass transfer between the zeolite crystallites of a membrane (intercrystalline transport route) can also take place in addition to mass transfer through the zeolite pores (intracrystalline transport route). They also show, for a silicalite membrane by pervaporation measurements using ethanol/water mixtures, that these intercrystalline transport routes can also be selective. Whether and how these intercrystalline transport routes can be influenced is not described.

Xomeritakis et al. state, in Ind. Eng. Chem. Res. 40 (2001), pages 544-552, that, in the separation of o-xylene and p-xylene using membranes of the MFI type, there is a further microporous transport route, for example at the particle boundaries, in addition to transport through zeolite pores and transport through mesoporous and macroporous defects of the membrane. Evidence of this transport route is provided from permeation measurements by adding n-hexane to a feed mixture comprising o-xylene and p-xylene. A method for influencing the formation of these microporous transport routes during the membrane production itself is not described.

It was therefore the object to provide a process by means of which the formation of microporous selective transport routes in the separation layer of MFI-containing membranes can be influenced and hence selectivity and permeability improved.

It was found that the object can be achieved by the addition of certain substances in the hydrothermal synthesis of the separation layer. The invention therefore relates to a process for the production of a composite membrane, one or more microporous separation layers comprising a zeolite of the MFI type being produced by hydrothermal synthesis on a porous substrate, wherein one or more additives from the group consisting of linear ($C_1$-$C_4$)-alcohols, ammonia, primary, secondary and tertiary amines having in each case ($C_1$-$C_4$)-alkyl radicals, ($C_1$-$C_4$)-amino alcohols and ($C_3$-$C_4$)-ketones are added to the synthesis solution for the hydrothermal synthesis.

By adding the additives according to the invention, the formation of microporous transport routes can be influenced in a targeted manner during the membrane production.

On addition of the additives according to the invention in suitable amounts, smaller crystallites are formed, which leads to an enlargement of the particle interface and influences the transport properties at the particle boundaries without the layer adhesion becoming insufficient.

The membranes produced according to the invention are distinguished by increased permeabilities for the desired molecules in combination with good selectivity.

The invention furthermore relates to a composite membrane obtainable by the process described above.

The invention furthermore relates to the use of a composite membrane obtainable by the process described above for separating substances by vapor permeation, gas permeation or pervaporation and for the filtration of liquids.

The term "microporous" is used in the sense of the IUPAC "Recommendations for the characterization of porous solids" Pure & Appl. Chem., 66 (1994), pages 1739-1758. Thus, microporous means that the pores have a size of less than 2 nm.

Suitable substrates are bodies having continuous pores with pore diameters of from 1 to 10 μm, which have, for example, the form of flat disks, tubes or capillaries. The form of so-called multichannel elements which are used in ceramic membranes for microfiltration or ultrafiltration is also advantageous. Independently of the geometrical form of the substrate, a so-called asymmetric structure of the substrate is preferred, in which this consists of a plurality of successive layers having decreasing pore diameter, the smallest pore diameter being present on that side of the substrate which is to be provided with the separation layer. This is preferably from 0.5 to 100 nm, particularly preferably from 1 to 60 nm. Suitable material for the substrate is a multiplicity of materials, such as, for example steels or oxide ceramic materials, such as, for example alumina, titanium dioxide or mixtures of metal oxides consisting predominantly of titanium dioxide, but silica, zirconium dioxide, magnesium oxide or other metal oxides are also suitable, provided that they have low water solubility.

Preferably, the substrate is provided with a suitable auxiliary layer, particularly preferably a gas-tight and alkali-resistant glass solder known per se, in the areas where the membrane projecting from it is brought into contact with a sealing material.

Said substrate is expediently cleaned before the further operations (for example by washing with acidic and/or alkaline aqueous $H_2O_2$ solutions). A subsequent drying step is also advantageous.

The hydrothermal synthesis is preferably carried out in a manner known per se to the person skilled in the art.

It can be carried out on the one hand in such a way that it is effected without further pretreatment directly on the substrate. However, it can also be effected by a seeding step in which a layer of seed particles which completely or partly covers that side of the substrate which is to be coated is applied to said side. The seed particles may be amorphous or crystalline bodies having particle sizes of from 1 to 1000 nm, which correspond in their chemical composition substantially to the separation layer to be synthesized; in a preferred variant, they consist of MFI zeolite.

The seeds are prepared by a separate hydrothermal process. The synthesis solution preferably has the following composition:

100 mol of $SiO_2$/from 0 to 1 mol of $Na_2O$, preferably from 0 mol to 0.4 mol of $Na_2O$/from 4 mol to 40 mol of TPAOH, preferably from 30 mol to 40 mol of TPAOH (tetrapropylammonium hydroxide)/from 0 mol to 36 mol of TPABr (TPABr=tetrapropylammonium bromide), preferably from 0 to 10 mol of TPABr, where TPAOH+TPABr should be $\leq 36$ mol/from 800 mol to 10 000 mol of $H_2O$/from 400 mol to 800 mol of ethanol, preferably 400 mol of ethanol, TEOS (tetraethyl orthosilicate) being used as the $SiO_2$ source.

Said tetrapropylammonium salts serve as structure-imparting agents (templates). Instead, it is also possible to use other templates, e.g. 1,6-hexanediol and piperazine, and a detailed description is to be found in: R. Szostak: Handbook of Molecular Sieves, page 521.

The solution is slowly stirred or left to stand in a closed autoclave container for from 10 to 500 hours at from 60° C. to 100° C., preferably at from 60° C. to 80° C. The further processing of the suspension is effected by dilution with demineralized water or by centrifuging to remove the solid, washing several times and subsequent redispersion in demineralized water which has been adjusted to pH 10 to pH 12 with NaOH or to pH 7-10 with $NH_3$ or water.

The application of the seed particles to the substrate can be effected in various ways: firstly, this can be done by slip casting, i.e. a preferably aqueous solution comprising the seed particles is brought into contact with that side of the substrate which is to be coated and, either as a result of applying excess pressure to the side to be coated relative to the side not to be coated or as a result of capillary suction exerted by the pores, the solution surrounding the seed particles is introduced into the pores while the seed particles, if they are larger than the pores, accumulate on that side of the substrate which is to be coated.

Secondly, however, the adhesion of the seed particles to the substrate can also be effected by a suitable assistant. Mono- or polymeric quaternary ammonium salts, such as, for example, poly-DADMAC (Redifloc®), (DADMAC=diallyldimethylammonium chloride), are particularly suitable here.

In general, mixtures known per se to the person skilled in the art are used as synthesis solutions for the hydrothermal synthesis (referred to below as "synthesis" for short). On the one hand, mixtures suitable for the formation of an MFI zeolite having a high pro-portion of silicon (high silica zeolite), i.e. of $20 < SiO_2 - Al_2O_3 < \infty$ are preferred. Silicalite is particularly preferred.

The preparation of such zeolites is described in WO-A 2005/068057, which is hereby incorporated by reference and by citation is considered to be part of this description.

Zeolites having a higher proportion of aluminum, in particular ZSM 5, are also preferred.

The synthesis solutions comprise in particular the following molar constituents, A being the additive according to the invention:

$SiO_2/Al_2O_3/Na_2O/TPAOH/TPABr/H_2O/A=1/5\times10-5$ to $5\times10-2$, preferably $6\times10-5$ to $1\times10-2$/from 0 to 0.2, preferably from 0.005 to 0.02/from 0 to 0.1, preferably from 0.03 to 0.08/from 0 to 0.1, preferably from 0.03 to 0.08/from (10-y) to (100-y), preferably from (20-y) to (50-y)/y with $0 < y \leq 50$.

If appropriate, the synthesis solution may also comprise isopropanol.

Among the alcohols, preferred additives A according to the invention are methanol, ethanol, n-propanol and n-butanol, particularly preferably methanol and ethanol. Preferred among the amines are primary and secondary, particularly preferably primary, amines. The alkyl radicals on the amines are preferably methyl and ethyl and n-propyl groups. n-Propylamine is particularly preferred. Also preferred is ammonia. A preferred aminoalcohol is ethanolamine. A preferred ketone is acetone. Particularly preferred additives A are methanol, ethanol, n-propanol and n-propylamine. It is also possible to use mixtures of two or more additives according to the invention.

The molar proportion of the additive A in the synthesis solution y is preferably 15-35, particularly preferably 20-35 and very particularly preferably 25-35.

The molar ratio of $H_2O$ and A in the synthesis solution is in general 100-1:1, preferably 10-2:1, particularly preferably 5-2:1.

Said tetrapropylammonium salts serve as structure-imparting agents (templates). Instead, it is also possible to use other templates, e.g. 1,6-hexanediol and piperazine, and a detailed description is to be found, for example, in: R. Szostak: Handbook of Molecular Sieves, page 521.

The $SiO_2$ source is in general a colloidal silica sol, such as, for example Levasil (from H. C. Starck) or an organosilicon compound, such as, for example TEOS (tetraethyl orthosilicate).

In the context of the invention, the terms "addition" and "to add" mean, in relation to the additives A according to the invention, an addition of the additive in free form to the synthesis solution.

With the use of, for example, organosilicon compounds as an $SiO_2$ source, a compound A bound in stoichiometric amounts may be present in the synthesis batch itself, which compound is liberated in the course of the synthesis. For example, with the use of TEOS, four equivalents of ethanol are liberated, which corresponds to a y value of 4.

In this case too, the transport through intercrystalline transport routes can be influenced in a targeted manner by the process according to the invention.

This can be effected by adding the corresponding additive to the synthesis batch or by removing the corresponding additive from the synthesis batch. For example, with the use of TEOS as an $SiO_2$ source, values of y >4 result on addition of ethanol and values of y <4 result through removal of ethanol, for example by rotary evaporation under reduced pressure.

If appropriate, the aluminum present in said silicate or an organoaluminum compound, such as, for example, aluminum isopropylate, or a soluble aluminum salt, such as aluminum chloride, nitrate or sulfate, may serve as an $Al_2O_3$ source.

The water used is preferably a water desalinated by means of ion exchangers, particularly preferably a water desalinated by means of ion exchangers with subsequent distillation at least once.

The synthesis solution is prepared, for example, by a procedure in which water, the additive according to the invention, TPAOH, TPABr and, if appropriate, the aluminum source are premixed and are stirred for from 1 to 120 min, preferably from 5 to 60 min, and the $SiO_2$ source is then introduced in dissolved, colloidal or suspended form in the course of from 1 to 100 min, particularly from 2 to 50 min. With the use of TEOS as an Si source, it is first hydrolyzed with water and a portion of the template and, if appropriate, then combined with the Al source, the alkali, the residual template and the residual water.

The solution is then stirred for a further 1 to 200 min, preferably 5 to 100 min and aged for from 1 to 150 min, preferably from 5 to 50 min, without stirring. During the abovementioned steps, the temperature is kept at from 5 to 100° C., preferably from 15 to 40° C.

A synthesis batch according to the invention can also be prepared by a procedure in which water, TPAOH, TPABr and, if appropriate, the aluminum source are premixed and are stirred for from 1 to 120 min, preferably from 5 to 60 min, and the $SiO_2$ source is then introduced in dissolved, colloidal or suspended form in the course of from 1 to 100 min, preferably from 2 to 50 min.

The solution is then stirred for a further 1 to 200 min, preferably 5 to 100 min, and aged for from 1 to 150 min, preferably from 5 to 50 min, without stirring.

Only after hydrolysis is complete is the additive according to the invention added to the synthesis batch or, if a corresponding compound forms in stoichiometric amounts by the hydrolysis with the use of an organosilicon compound as an $SiO_2$ source, amounts smaller than the amount formed stoichiometrically by the $SiO_2$ source can be established by removing the compound.

During said steps, the temperature is kept at from 5 to 100° C., preferably from 15 to 40° C.

This is followed by the actual synthesis in which the solution is brought into contact with the seeded substrate over a period of from 1 to 100 h, preferably from 5 to 50 h, particularly preferably from 10 to 20 h, the synthesis temperature being from 100 to 250° C., preferably from 140 to 210° C., particularly preferably from 170 to 190 degrees. Bringing into contact can be effected in various ways: thus, during the synthesis time, the synthesis solution can be substantially stagnant or it can be removed steadily or at regular or irregular intervals in the same direction or changing directions over the substrate to be coated. A procedure which ensures that the synthesis solution comes into contact predominantly with the surfaces of the substrate which are to be coated and less with the opposite site is advantageous. If coating of the inside is desired, for example in the case of a tubular membrane, it is advantageous to make it more difficult for the synthesis solution to come into contact with the outside of the tube. This can be achieved firstly if the surface(s) not to be coated are covered in a suitable manner by a removable layer poorly permeable in the synthesis solution. In the case of the tube to be coated on the inside, this covering layer may be a winding with a tape, e.g. of PTFE or a suitable polymer solution which can be brushed on. Secondly, the access of the synthesis solution to the surface(s) not to be coated can, however, also be made more difficult by filling the pores of the substrate during the synthesis with a medium which impedes or prevents the passage of the synthesis solution through the pores of the substrate, as described in WO 2005/068056 A1. This medium may be

- a liquid in which the synthesis solution is only poorly soluble or
- a solid which is introduced as a melt into the pores of the substrate and, after the end of the synthesis, is removed by melting or dissolution with a suitable solvent or
- a gas, e.g. air or nitrogen, which is present in the space adjacent to the surface(s) not to be coated and at least partly in the pores of the substrate, the pressure of the gas being adjusted so that passage of the synthesis solution from the side to be coated to that side of the substrate which is not to be coated is suppressed.

It is advantageous to carry out the preparation of the seeds and of the synthesis solution and the hydrothermal synthesis itself in vessels which can release virtually no aluminum to the solutions. Low-Al steels and/or organic polymers, such as, for example, PTFE, PFA, (PTFE=polytetrafluoroethylene, PFA=perfluoroalkoxy copolymers), polypropylene or materials which are coated with at least one of said materials on the surfaces coming into contact with the solution are particularly suitable.

After the synthesis, washing once or several times with water or an acidic solution is advantageous for removing traces of alkali. The acidic solution may comprise aqueous solutions of inorganic or organic acids, such as acetic or formic acid, the acid concentration being from $10^{-5}$ to 1 mol/l, preferably from $10^{-4}$ to 0.01 mol/l, and the duration of the washes being from 5 to 120 min, preferably from 10 to 90 min.

In general, drying at a temperature of from 5 to 40° C. for from 1 to 100 h, preferably from 10 to 30 h, is then effected, a flowing or stationary gas, preferably nitrogen or air, being present above the material being dried.

After the drying, the membrane is generally calcined by heating at a heating rate of from 0.1 to 1 K/min to a temperature of from 200 to 600 degrees, preferably from 350 to 500° C., a hold time of from 100 to 500 min possibly being advantageous at an intermediate temperature of from 300 to 400° C.

At the end temperature, a residence time of from 30 min to 300 min is maintained and cooling is then effected at a rate of from 0.1 K/min to 10 K/min.

The membrane thus produced can be subjected to a further treatment step in which at least one further layer is applied for producing a cohesive zeolite layer.

The membrane is preferably used in modules into which in each case at least one of the membranes described is sealed so that the MFI layer separates the feed space from the permeate space. If the membranes are present in the form of tubes or multichannel elements, the sealing in can be effected by means of O-rings comprising elastomers or by casting the elements in a polymeric or ceramic casting compound at at least one end of the elements and subsequently cutting off the casting compound. Casting in at only one end is expedient in the case of tubular modules in which the feed space is present on the outside of the tube and in which the tubes are closed at the end not sealed in.

Preferably, one or more of the modules described are a component or components of a membrane unit. This may be operated by a plurality of methods known per se to the person skilled in the art, either for gas separation, in which the feed stream is brought into contact in gaseous form with the membrane, or for pervaporation, the mixture (feed) to be separated being brought into contact in liquid form with the membrane and the stream (permeate) passing through the membrane being taken off in gaseous form. The temperature at which the mixture to be separated is brought into contact with the membrane is in general from 20 to 300° C., preferably from 50 to 200° C. The pressure on the feed side of the membrane is in general from 1 to 100, preferably from 1 to 35, bar abs. The pressure on the permeate side is from 1 to 20 000, preferably from 10 to 0 000, mbar abs., the pressure on the feed side generally being higher than on the permeate side. The pressure on the permeate side is established by removing the permeate stream by means of a vacuum pump and/or of a compressor and/or by condensation of the permeate stream at a temperature which leads to an intrinsic pressure of the permeate mixture which corresponds to the desired permeate pressure. However, it is also possible to reduce the partial pressure of the permeating components by introducing a sweep gas on the permeate side. Suitable sweep gases are, for example, nitrogen or steam.

In the case of pervaporation, it may be advantageous to divide the required membrane area over a plurality of apparatuses and, to compensate for the heat loss caused by the liquid-gas phase transition, to connect one or more heat exchangers between the membrane apparatuses.

However, the membrane unit can also be operated by a vapor permeation method known per se to the person skilled in the art, which vapor permeation differs from per-vaporation in that the feed is brought into contact with the membrane in vapor form.

The membrane process can on the one hand be carried out in one stage, i.e. both the retentate and the permeate from one membrane apparatus or the combined permeates from a plurality of membrane apparatuses through which the feed flows in succession and/or in parallel leave the membrane unit without further treatment. However, the membrane process can also be carried out in two or more stages, the permeate being led from one stage as feed into the respective following stage, and the retentate from this stage being mixed with the feed into the first-mentioned stage. Such arrangements are known per se (see, for example Sep. Sci. Technol. 31 (1996), 729 et seq.).

The composite membranes according to the invention are suitable for separating substances by vapor permeation, gas permeation or pervaporation and for the filtration of liquids.

Preferably, the composite membranes are suitable for the separation of hydrocarbon mixtures, particularly preferably of isomeric linear and branched hydrocarbons, in particular n-butane and isobutane, or n-butene and isobutene.

Liquids having different polarities can be separated by pervaporation, for example alcohols and water, in particular ethanol/water or isopropanol/water mixtures.

The invention is explained by the following examples:

EXAMPLE 1 a) Pretreatment of the Substrates:

Three porous substrates in tubular form (length 250 mm, external diameter 10 mm, internal diameter 6 mm, pore size on the inside 5 nm, provided with glass solder at the ends) comprising $TiO_2$ were first with seeds (silicalite crystals having a size of 30-100 nm) by means of slip casting. Thereafter, the tube was heated at a rate of 0.75 K/h to 400° C., kept at 400° C. for 7 h and then cooled at a rate of 0.75 K/h to room temperature. Thereafter, the tube was wound on the outside with PTFE tape and placed in a synthesis solution prepared according to the following description.

b) Preparation of the Synthesis Solution:

The composition of the synthesis solutions is stated in the table. The source for $SiO_2$, $Al_2O_3$ and $Na_2O$ was the silica sol Levasil® 300/30% (from Kurt Obermeier, Bad Berleburg, Germany), having an $SiO_2/Al_2O_3/Na_2O$ ratio of 90/0.15/1.66. Water (purified by ion exchange and double distillation), TPAOH (40% strength aqueous solution, from Alfa Aesar), TPABr (from Merck) and the additive according to the invention as stated in the table were introduced into a polypropylene conical flask and stirred at room temperature for 30 min. The Levasil was then added dropwise with stirring.

| Membrane | Molar ratio in the synthesis solution[1] | Type of additive |
|---|---|---|
| 1 | 90/0.225/1/4.15/1.85/1990/0 | no additive |
| 2 | 90/0.225/1/4.15/1.85/1490/500 | methanol |
| 3 | 90/0.225/1/4.15/1.85/1490/500 | ethanol |
| 4 | 90/0.225/1/4.15/1.85/1490/500 | n-propanol |
| 5 | 90/0.225/1/4.15/1.85/1490/500 | ethanolamine |
| 6 | 90/0.225/1/4.15/1.85/1490/500 | n-propylamine |
| 7 | 90/0.225/1/4.15/1.85/1790/200 | ethanol |
| 8 | 90/0.225/1/4.15/1.85/1640/350 | ethanol |
| 9 | 90/0.225/1/4.15/1.85/1390/600 | ethanol |

[1] $SiO_2/Al_2O_3/Na_2O/TPAOH/TPABr/H_2O$/additive c) Hydrothermal Synthesis:

The syntheses were effected at a temperature of 180° C. for a duration of 24 h by placing the cold autoclave with the synthesis solution and the seeded substrate wound with Teflon tape on the outside in a pretreated drying oven. After the synthesis, the Teflon tape was removed.

d) Aftertreatment:

The membrane was placed in a measuring cylinder and washed 4 times alternately with 0.1 M formic acid and water in each case for 30 min with stirring. Thereafter, the membranes were left to dry for about 16 h in the room air and then introduced into a through-circulation oven and first heated at a rate of about 0.3 K/h to 450° C. and left there for 400 min. Cooling was then effected at a rate of 17 K/h to room temperature.

e) Permeation Experiments:

For the permeation experiments, the membranes were placed in a test module. The sealing of the feed space from the permeate space was achieved by means of an O-ring seal. The O-rings were pushed over the glazed ends of the substrate.

The test module was placed in an oven.

Before the measurements, the membranes were evacuated and the feed lines and the oven preheated to 130° C. The individual gas flow rates of $H_2$, $N_2$, 1-butene and isobutene were then determined. After each individual gas measurement, the feed space and permeate space were evacuated.

The test gas was a 50/50 1-butene/isobutene mixture (from Linde, purity of the gases in each case 99.5%), present in a gas cylinder. This test gas flowed form the gas cylinder to the test module on the feed side. After the test module, the pressure on the feed side was adjusted to 2.5 bar abs. by means of an after-pressure regulator. The measurement of the amount of permeate and amount of retentate was effected via commercially available soap bubble counters.

During the permeation measurements, the temperature of the test module was kept at 130° C.

The permeate stream leaving the test module (permeate pressure: about 1 bar abs.) was passed into the sampling loop of a GC-MS apparatus and analyzed there.

The results of the measurements are shown in the following table (1-butene permeance $J_{1\text{-}butene}$ and permselectivity PS). The permeance of a component i is the local permeate flow density of the component i divided by the partial pressure difference between feed side and permeate side of component i. The permselectivity is the ratio of the permeances.

| Membrane | $J_{1\text{-}butene}$ in $m^3_N/(m^2\, h\, bar)$ | PS |
|---|---|---|
| 1 | 0.66 | 22.0 |
| 2 | 1.39 | 22.8 |
| 3 | 1.72 | 18.9 |
| 4 | 1.83 | 13.3 |
| 5 | 1.11 | 15.7 |
| 6 | 2.39 | 12.4 |
| 7 | 1.56 | 11.4 |
| 8 | 1.48 | 14.4 |
| 9 | 2.76 | 9.2 |

The results show that the transport properties of the zeolite membranes can be influenced in a targeted manner by addition of various additives. A very large increase in the 1-butene permeances is achievable, no loss or only a small loss of selectivity having to be accepted.

f) Pervaporation Experiments:

For pervaporation experiments, membrane 3 was placed in a test module. A mixture of ethanol and water having a proportion of 5% by weight of ethanol was fed in liquid form to the membrane at a temperature of 40° C. The permeate pressure was 13 mbar. The measurements gave a permeate flow of 0.8 kg/(m² h). The ethanol concentration in the permeate was 68% by weight.

We claim:

1. A process for the production of a composite membrane comprising at least one microporous separation layer comprising a zeolite of the MFI type on a porous substrate, comprising:

contacting a surface of the porous substrate in a hydrothermal treatment with a synthesis solution comprising at least one additive selected from the group consisting of linear $(C_1\text{-}C_4)$-alcohols, ammonia, primary, secondary and tertiary amines having in each case $(C_1\text{-}C_4)$-alkyl radicals, ethanolamine and $(C_3\text{-}C_4)$-ketones are added to the synthesis solution for the hydrothermal synthesis, wherein the synthesis solution has the following molar constituents, with A being said at least one additive:

$SiO_2/Al_2O_3/Na_2O/TPAOH/TPABr/H_2O/A = 1/5 \times 10^{-5}$ to $5 \times 10^{-2}$ /from 0 to 0.2/from 0.03 to 0.08/from 0.03 to 0.08/from (10−y) to (100−y)/y with $0 < y \leq 50$, wherein the molar ratio of $H_2O$ to additive A in the synthesis solution is 100−1 : 1.

2. The process according to claim 1, wherein one or more compounds selected from the group consisting of methanol, ethanol, n-propanol, n-butanol, primary amines having $(C_1\text{-}C_4)$-alkyl groups, ammonia and acetone are added as the additive.

3. The process according to claim 2, wherein one or more compounds selected from the group consisting of methanol, ethanol, n-propanol and n-propylamine are added as the additive.

4. The process according to claim 1, wherein y has a value ranging from 15 to 35.

5. The process according to claim 1, wherein a plurality of zeolite layers is applied to the substrate.

6. A composite membrane obtainable by the process according to claim 1 having microporous transport routes.

7. A method of separating substances, comprising:
separating a substance by vapor permeation, gas permeation or pervaporation and by the filtration of liquids through the composite membrane of claim 6.

8. The method according to claim 7, wherein butane/isobutane or butene/isobutene mixtures are separated.

9. The method according to claim 7, wherein ethanol/water mixtures are separated.

10. The method according to claim 7, wherein isopropanol/water mixtures are separated.

* * * * *